(12) United States Patent
Min et al.

(10) Patent No.: US 12,285,604 B2
(45) Date of Patent: *Apr. 29, 2025

(54) IMPLANTATION MEDICAL DEVICE WITH MULTIPLE PARASTERNAL-ANTERIOR ELECTRODES

(71) Applicant: Pacesetter, Inc., Sylmar, CA (US)

(72) Inventors: Xiaoyi Min, Simi Valley, CA (US); Kyungmoo Ryu, Palmdale, CA (US); Keith Victorine, Santa Clarita, CA (US); Stuart Rosenberg, Castaic, CA (US); Gene A. Bornzin, Simi Valley, CA (US)

(73) Assignee: Pacesetter, Inc., Sylmar, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/437,198

(22) Filed: Feb. 8, 2024

(65) Prior Publication Data

US 2024/0181250 A1 Jun. 6, 2024

Related U.S. Application Data

(63) Continuation of application No. 17/683,249, filed on Feb. 28, 2022, now Pat. No. 11,931,568, which is a
(Continued)

(51) Int. Cl.
*A61N 1/05* (2006.01)
*A61N 1/39* (2006.01)

(52) U.S. Cl.
CPC ......... *A61N 1/0587* (2013.01); *A61N 1/0504* (2013.01); *A61N 1/3918* (2013.01); *A61N 1/3956* (2013.01)

(58) Field of Classification Search
CPC .. A61N 1/0587; A61N 1/0504; A61N 1/3918; A61N 1/3956
See application file for complete search history.

(56) References Cited

U.S. PATENT DOCUMENTS 6,866,044 B2 3/2005 Bardy et al.
7,149,575 B2 12/2006 Ostroff et al.
(Continued)

FOREIGN PATENT DOCUMENTS

CN 107567304 A 1/2018
EP 3493877 B1 5/2020

OTHER PUBLICATIONS

De Maria et al.; "The Entirely Subcutaneous Defibrillator (S-ICD): State of the Art and Selection of the Ideal Candidate" Current Cardiology Reviews; 2015; 7 pages.
(Continued)

*Primary Examiner* — Paula J Stice
(74) *Attorney, Agent, or Firm* — Dean D. Small; The Small Patent Law Group, LLC

(57) ABSTRACT

A subcutaneous implantable medical device and method (SIMD) provided. A pulse generator (PG) is configured to be positioned subcutaneously within a lateral region of a chest of a patient. The PG has a housing that includes a PG electrode. The PG has an electronics module. An elongated lead is electrically coupled to the pulse generator. The elongated lead includes a first electrode that is configured to be positioned along a first parasternal region proximate a sternum of the patient and a second electrode that is configured to be positioned at an anterior region of the patient. The first and second electrodes are coupled to be electrically common with one another. The electronics module is configured to provide electrical shocks for antiarrhythmic therapy along at least one shocking vector between the PG electrode and the first and second electrodes.

18 Claims, 6 Drawing Sheets

Related U.S. Application Data continuation of application No. 16/983,053, filed on Aug. 3, 2020, now Pat. No. 11,291,834, which is a continuation of application No. 15/973,195, filed on May 7, 2018, now Pat. No. 10,765,860.

(56) References Cited

U.S. PATENT DOCUMENTS

| | | | |
|---|---|---|---|
| 7,536,222 | B2 | 5/2009 | Bardy et al. |
| 7,655,014 | B2 | 2/2010 | Ko et al. |
| 7,774,059 | B2 | 8/2010 | Ostroff et al. |
| 8,831,720 | B2 | 9/2014 | Bardy et al. |
| 9,220,913 | B2 | 12/2015 | Christie et al. |
| 9,295,834 | B2 | 3/2016 | Wulfman et al. |
| 9,610,436 | B2 | 4/2017 | Seifert et al. |
| 10,244,957 | B2 | 4/2019 | Zhang |
| 10,449,362 | B2 | 10/2019 | Anderson et al. |
| 10,471,267 | B2 | 11/2019 | Thompson-Nauman et al. |
| 10,525,272 | B2 | 1/2020 | Thompson-Nauman et al. |
| 10,556,117 | B2 | 2/2020 | Thompson-Nauman et al. |
| 11,045,643 | B2 | 6/2021 | Fischer et al. |
| 11,484,705 | B2 | 11/2022 | Min et al. |
| 11,590,353 | B2 | 2/2023 | Koop et al. |
| 2002/0035380 | A1 | 3/2002 | Rissmann et al. |
| 2002/0049475 | A1 | 4/2002 | Bardy et al. |
| 2003/0036778 | A1 | 2/2003 | Ostroff et al. |
| 2012/0203297 | A1 | 8/2012 | Efimov et al. |
| 2016/0121106 | A1 | 5/2016 | Marshall et al. |
| 2016/0121130 | A1 | 5/2016 | Cinbis et al. |
| 2016/0175601 | A1 | 6/2016 | Nabutovsky et al. |
| 2016/0213920 | A1 | 7/2016 | Rosenberg et al. |
| 2019/0054297 | A1 | 2/2019 | Zhang et al. |
| 2020/0282226 | A1 | 9/2020 | Rosenberg et al. |

OTHER PUBLICATIONS

Kempa et al.; "Implantation of additional Subcutaneous Array Electrode Reduces Defibrillation Threshold in ICD Patients—Preliminary Results" Archives of Medical Science: AMS; 2012; 5 pages.

Payne et al. "Relationship of Shock Energy to Impedance During Subcutaneous Implantable Cardioverter-Defibrillator Testing" Circulation: Arrhythmia and Electrophysiology; Sep. 2020 (3 pages).

Amin et al. "Factors Associated with High-Voltage Impedance and Subcutaneous Implantable Defibrillator Ventricular Fibrillation Conversion Success" Circulation: Arrhythmia and Electrophysiology; Apr. 2019 (10 pages).

IMPLANTATION MEDICAL DEVICE WITH MULTIPLE PARASTERNAL-ANTERIOR ELECTRODES

REFERENCE TO RELATED APPLICATIONS

The present application is a continuation of, and claims priority to U.S. application Ser. No. 17/683,249, filed 28 Feb. 2022, which is a continuation application of, and claims priority to, U.S. application Ser. No. 16/983,053, filed on 3 Aug. 2020 (now U.S. Pat. No. 11,291,834, issued 5 Apr. 2022), which is a continuation application of, and claims priority to, U.S. application Ser. No. 15/973,195, filed on 7 May 2018, (now U.S. Pat. No. 10,765,860, issued 8 Sep. 2020) the complete subject matter of which are expressly incorporated herein by reference in their entirety.

BACKGROUND

Embodiments of the present disclosure relate generally to subcutaneous implantable medical devices and methods, and more particularly to medical devices having pulse generators and leads that are implanted subcutaneously.

Currently, implantable medical devices (IMD) are provided for a variety of cardiac applications. IMDs may include a "housing" or "canister" (or "can") and one or more electrically-conductive leads that connect to the canister through an electro-mechanical connection. IMDs may contain electronics (e.g., a power source, microprocessor, capacitors, etc.) that control electrical activation of the leads to provide various functionalities. For instance, the IMD may be configured for pacemaking, cardioversion, and/or defibrillation. An implantable cardioverter-defibrillator (ICD) is one such medical device and it is designed to monitor heart rate, recognize certain events (e.g., ventricular fibrillation or ventricular tachycardia), and deliver electrical shock to reduce the risk of sudden cardiac death (SCD) from these events. The ICD may be used for patients who have already experienced potentially life-threatening events or for those that are at risk of SCD. The ICD includes a pulse generator and one or more leads having electrodes that may be used to detect how the heart is functioning or provide electrical shock to the heart.

One type of ICD delivers therapy through transvenous leads that are advanced to the right ventricle for detection and treatment of tachyarrhythmia. Transvenous ICDs (or TV-ICDs) may also provide bradycardia-pacing support. Although TV-ICDs can be helpful and prevent sudden cardiac death, TV-ICDs may have certain drawbacks or potential complications. For instance, it can be difficult and time-consuming to achieve venous access, thereby prolonging the medical procedure. TV-ICDs can be associated with hemopericardium, hemothorax, pneumothorax, lead dislodgement, lead malfunction, device-related infection, and venous occlusion. Transvenous leads may also malfunction through conductor failure in the leads or breaches in the insulation that surrounds the conductors.

A second type of ICD, referred to as a subcutaneous ICD (or S-ICD), uses an electrode configuration that can reside entirely within the subcutaneous space. The pulse generator is positioned along a side of the patient's chest below the arm pit (e.g., over the sixth rib near the left mid-axillary line). A lead extends from the pulse generator along the side of the patient toward the sternum. The lead then turns to extend parallel to the mid-sternal line and is positioned adjacent to the sternum extending between the xiphoid process and the manubriosternal junction. This portion of the lead includes a shock coil that is flanked by two sensing electrodes. The sensing electrodes sense the cardiac rhythm and the shock coil delivers counters-hocks through the subcutaneous tissue of the chest wall. Unlike the transvenous types, the S-ICDs lack intravenous and intracardiac leads and, as such, are less likely to have the noted complications associated with more invasive devices. Current electrode configurations for S-ICDs, however, have some challenges or undesirable features. For instance, conventional commercially available as ICDs are relatively large and exhibit higher defibrillation threshold (DFTs), as compared to modern transvenouSIMDs. For example, a conventional S-ICD may be 60-70 mL in volume, as compared to a 30 mL transvenouSIMD. As another example, a conventional S-ICD may utilize DFTs of 80 J, as compared to 40 J for transvenouSIMDs. A desire remains to further improve upon the size and energy demands of S-ICDs.

SUMMARY

In accordance with embodiments herein, a subcutaneous implantable medical device (SIMD) is provided. A pulse generator (PG) is configured to be positioned subcutaneously within a lateral region of a chest of a patient. The PG has a housing that includes a PG electrode. The PG has an electronics module. An elongated lead is electrically coupled to the pulse generator. The elongated lead includes a first electrode that is configured to be positioned along a first parasternal region proximate a sternum of the patient and a second electrode that is configured to be positioned at an anterior region of the patient. The first and second electrodes are coupled to be electrically common with one another. The electronics module is configured to provide electrical shocks for antiarrhythmic therapy along at least one shocking vector between the PG electrode and the first and second electrodes.

Optionally, the anterior region may represent a second parasternal region. The second electrode may be configured to be oriented to extend in a common direction with the first electrode and along a midline of the sternum. The first and second electrodes may be configured to be spaced apart by a distance of between 1.5 cm and 8 cm as measured in a direction transverse to a midline of the sternum. The first and second electrodes may be configured to be positioned along opposite sides of the sternum and separated from one another by a predetermined distance. The first and second electrodes may be configured to be positioned on a common side of the sternum and separated from one another by a predetermined distance. At least one of the first and second electrodes may have an active length of 7-11 cm and the predetermined distance separating the first and second electrodes may be 6.0 to 8.5 cm.

Optionally, the anterior region may be located proximate to a lower end of the sternum. The second electrode may be configured to be oriented to extend in a non-parallel direction relative to a direction of the first electrode. The second electrode may be located at relative to a midline of the sternum that may be vertically below the first electrode. The first electrode may have a length that is greater than a length of the second electrodes. The length of the first electrode may be 7.0 cm to 11.0 cm, and the length of the second electrode may be 5.0 cm to 6.5 cm. The lead may include a lead body having a base segment with a proximal end to be electrically coupled to a header of the PG.

Optionally, the lead may include first and second distal branches at a distal end of the lead. The first and second electrodes may be provided on the first and second distal branches, respectively.

The lead body may further comprise a Y-connector connecting the first and second distal branches to a distal end of the base segment. The pulse generator and first and second electrodes may define a shocking vector that may provide to a defibrillation threshold of at most 20 Joules. The pulse generator and first and second electrodes may define a shocking vector there between that may exhibit an impedance along the shocking vector that is no more than 64 ohms. The pulse generator and first and second electrodes may define a shocking vector there between that may exhibit an impedance along the shocking vector that is no more than 56.2 ohms.

In accordance with embodiments herein, a method is provided. The method comprises implanting a pulse generator (PG) within a lateral region of a chest of a patient. The PG has a housing that includes a PG electrode. The method implants at least one lead having first and second electrodes that are coupled to be electrically common with one another. The first and second electrodes are elongated. The implanting comprising positioned the first electrode along a first parasternal region proximate to a sternum of the patient and positioning the second electrode at an anterior region of the patient. The method configures the electronics module to provide electrical shocks for antiarrhythmic therapy along at least one shocking vector between the PG electrode and the first and second electrodes.

Optionally, the method may comprise positioning the first and second electrodes at a dual parasternal position extending in a common direction and spaced apart by a distance of 1.5 cm to 8.5 cm. The method may comprise positioning the first and second electrodes along opposite sides of the sternum and positioning the first and second electrodes on a common side of the sternum. At least one of the first and second electrodes may have an active length of 8-11 cm and the predetermined distance separating the first and second electrodes may be 6.0 to 8.5 cm. The method may comprise positioning the second electrode proximate to a lower end of the sternum and orienting the second electrode to extend in a non-parallel direction relative to a direction of the first electrode, locating the second electrode at a position, relative to a midline of the sternum that may be vertically below the first electrode. The non-parallel direction may orient a longitudinal axis of the second electrode perpendicular to a longitudinal axis of the first electrode. The pulse generator may be configured to generate a defibrillating energy of at most 40 Joules.

DETAILED DESCRIPTION

Embodiments set forth herein include implantable medical devices (SIMDs) and methods of using and positioning the same. In particular embodiments, the SIMD includes a subcutaneous implantable cardioverter-defibrillator (S-ICD). Embodiments include a pulse generator that is positioned within a lateral region of a chest of a patient. The PG has a housing or canister that includes a PG electrode. Embodiments also include at least one lead having first and second electrodes with the first electrode positioned along a first parasternal region of the chest of the patient and the second electrode positioned along a second anterior region of the chest.

As used herein, the term "subcutaneously," when used to describe implanting a device (e.g., pulse generator, lead body, electrode, etc.), means implanting the device beneath the skin but above layers of skeletal muscle tissue, rib bones, and costal cartilage. The device is typically positioned under the subcutaneous tissue. When the term "subcutaneous" is used to characterize the entire implantable medical system, the term means that most of the operating components of the system (e.g., the pulse generator, shocking electrodes, optional sensing electrodes, lead bodies) or each and every one of the operating components is beneath the skin, but above layers of skeletal muscle tissue, rib bones, and costal cartilage. Compared to transvenous ICD implantation, subcutaneous implantation may be less complex, less invasive, and less time-consuming. In some embodiments, however, one or more components may not be subcutaneous.

The terms "vertical", "horizontal" and "lateral", as used in connection with describing electrode orientation and position, are used generally relative to a longitudinal axis extending through a patient chest and more specifically relative to an axis extending along a midline of a sternum of the patient's check. For example, the sternum shall be considered to extend in a "vertical" direction, regardless of whether the patient is in a standing, sitting, prone or other position. As further examples, the horizontal and lateral directions refer interchangeably to a direction that is perpendicular to the midline of the sternum.

Embodiments herein provide an SIMD that exhibits defibrillation thresholds (DFTs) that are less than conventional SIMDs. For example, the DFT in some embodiments is at most 22 Joules, and in other certain embodiments is at most 20 Joules or, more particularly, 10-20 Joules.

The terms "the lead" and "at least one lead" shall include only a single lead and more than one single lead. For the avoidance of doubt, when "the lead" or "at least one lead" is described to include first and second electrodes, it is understood that the first and second electrodes may be provided as a common single lead body or the first and second electrodes may be provided on different first and second lead bodies of first and second leads, respectively.

Figure 1A:
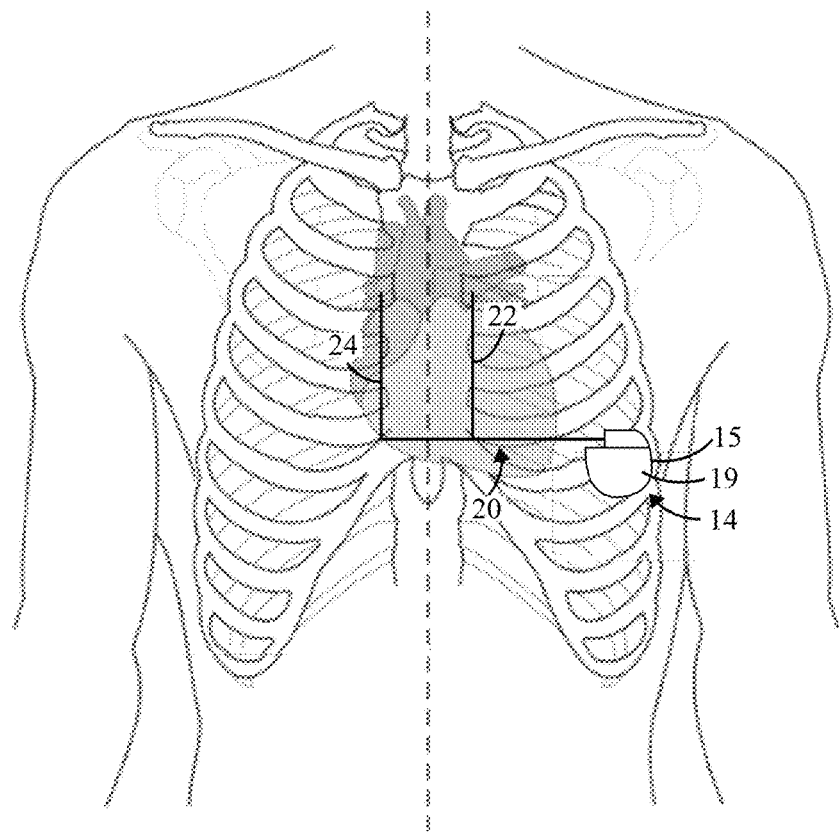
FIG. 1A illustrates a graphical representation of a subcutaneous implantable medical system that is configured to apply therapy to a heart in accordance with embodiments herein.
Figure 1B:
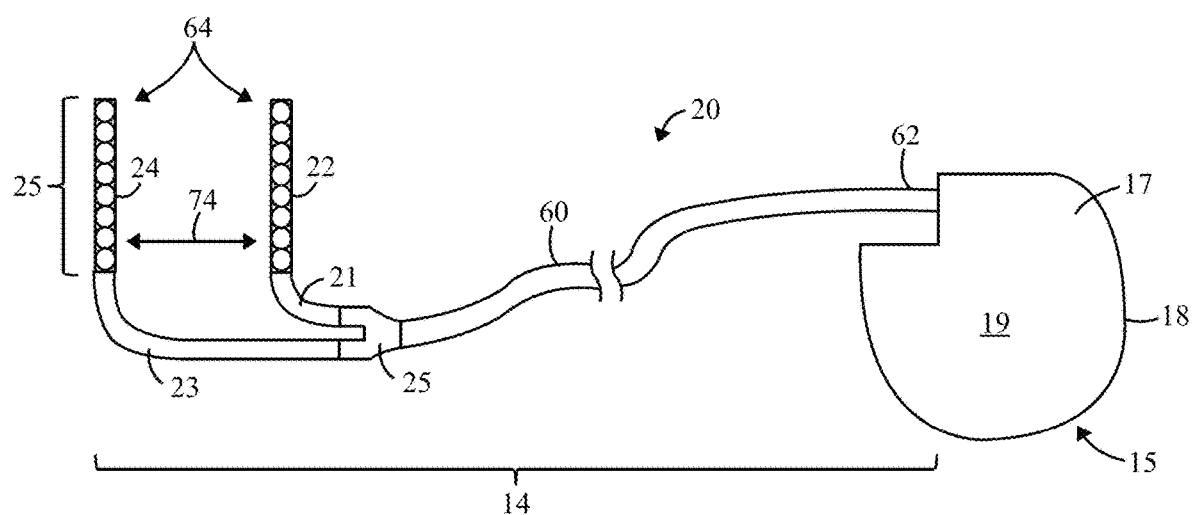
FIG. 1B illustrates a graphical representation of a subcutaneous implantable medical system that is configured to apply therapy to a heart in accordance with embodiments herein.

FIGS. 1A and 1B illustrate a graphical representation of a subcutaneous implantable medical system that is configured to apply therapy to a heart. FIG. 1A illustrates a torso of a patient to show the rib cage and a general outline of the heart and greater vessels. In particular embodiments, the system may apply high voltage defibrillation shocks, as well as other general arrhythmia therapy, such as pacing therapy, cardiac resynchronization therapy (CRT), and the like. The system includes a subcutaneous implantable medical device (SIMD) 14 that is configured to be implanted in a subcutaneous area exterior to the heart. The system includes only the SIMD and is entirely or fully subcutaneous. As shown in FIG. 1A, the SIMD 14 is positioned within a lateral region, such as along the left side of the rib cage under the left arm. The SIMD 14 may be positioned relative to a vertical direction substantially aligned with the apex of the heart. The SIMD 14 is configured to deliver various arrhythmia therapies, such as defibrillation therapy, pacing therapy, antitachycardia pacing therapy, cardioversion therapy, and the like. The system does not require insertion of includes a transvenous lead. It is contemplated, however, that system may include other components. For example, alternative embodiments may include a transvenous lead or a leadless electrode in addition to the structures in FIG. 1A.

The lead 20 includes at least two electrodes 22, 24 that are used for providing electrical shock for defibrillation. Optionally, the lead 20 may include one or more sensing electrodes. The pulse generator 15 may be implanted subcutaneously and at least a portion of the lead 20 may be implanted subcutaneously. In particular embodiments, the SIMD 14 is an entirely or fully subcutaneous SIMD. The pulse generator 15 may be positioned at a lateral position or below an apex of the heart.

With reference to FIG. 1B, the lead 20 includes an elongated lead body 60 that extends from a proximal end 62 to a distal tip 64. The pulse generator 15 includes a housing 18 that is configured to be active to form a pulse-generator (PG) electrode 19. The pulse generator 15 also includes a header 17 mounted to the housing 18. The header 17 is configured to receive and be connected to the proximal end 62 of the lead body 60. The proximal end 62 may include one or more contacts (not shown) that electrically engage respective terminals (not shown) in the header 17 of the pulse generator 15.

The elongated lead body 60 may be formed as a flexible tube or sleeve comprising, for example, a biocompatible material (e.g., polyurethane, silicone, etc.). The lead body 60 may include a single lumen (or passage) or multiple lumen (or passages) within the flexible tube. The lead 20 also includes a plurality of electrical conductors (not shown) that extend along the lumen and electrically couple the electrodes 22, 24 (and optionally sensing electrodes) to the pulse generator 15. The electrical conductors may be cabled conductors coated with PTFE (poly-tetrafluoroethylene) and/or ETFE (ethylenetetrafluoroethylene). The lead body 60 may be configured for receiving a stylet that enables positioning of the lead. The electrical conductors are terminated to the respective electrodes. For example, the conductors may be terminated to respective electrodes of the proximal end 62 and then respective electrodes 22, 24 (described below).

The lead body 60 may include one or more distal branches 21, 23 that separate from a splitting connector 25, where the distal branches 21, 23 each include a corresponding one of the electrodes 22, 24. As shown, the lead body 60 includes two distal branches 21, 23 and two electrodes 22, 24, although it is recognized that more than two branches and more than two electrodes may be provided on the lead body 60. Additionally or alternatively, two or more separate leads 20 may be provided, with each lead 20 having a single distal segment and single electrode provided thereon. For example, the electrodes 22 and 24 may be provided on separate leads that are individually joined to the header 17. The distal branches 21, 23 may have a common length or different lengths. For example, the distal branch 23 may be longer than the distal branch 21, such as when the electrode 24 is intended to be implanted at a location further from the pulse generator 15, as compared to the distance between the pulse generator 15 and the electrode 22. The splitting connector 25 may be configured in different shapes and different manners. For example, the splitting connector 25 may be formed as a Y-connector, a T-connector and the like. The splitting connector 25 may be formed as part of a monotonic unitary body structure with the lead body 60 and distal branches 21, 23. Optionally, the connector 25 may be formed as part of a monotonic unitary body structure with the lead body 60, but separate from the distal branches 21 and 23. For example, the distal branches 21 and 23 may include connector pins at the proximal ends thereof, where the connector pins are configured to be received into terminals within the connector 25. Optionally, the connector 25 may be formed as part of a monotonic unitary body structure with the distal branches 21, 23 and include a connector pin or terminal at the proximal end that is configured to join a mating terminal or connector pin on the distal end of the lead body 60. Providing a connection at the connector 25 enables different combinations of lead bodies 60 and distal branches 21, 23 to accommodate different implant locations and orientations, different shocking vectors and different anatomic dimensions.

The electrodes 22, 24 may be referred to as first and second electrodes 22, 24 that are coupled to be electrically common with one another. The first and second electrodes 22, 24 are elongated along corresponding longitudinal axes. During the implantation operation the implanting comprises positioned the first electrode 22 along a first parasternal region proximate to a sternum of the patient and positioning the second electrode 24 at an anterior region of the patient. The first and second electrodes 22, 24 may be positioned in a dual parasternal combination extending in a common direction and spaced apart by a distance of 1.5 cm to 8.5 cm. The positioning operation may comprise positioning the first and second electrodes 22, 24 along opposite sides of the sternum, or positioning the first and second electrodes 22, 24 on a common side of the sternum. At least one of the first and second electrodes 22, 24 has an active length of 8-11 cm. A predetermined spacing separates the first and second electrodes. The anterior positioning operation may comprise positioning the second electrode proximate to a lower end of the sternum and orienting the second electrode to extend in a direction non-parallel to a direction of the first electrode, and locating the second electrode at a position, relative to a midline of the sternum, that is vertically below the first electrode. The non-parallel direction may orient a longitudinal axis of the second electrode perpendicular to a longitudinal axis of the first electrode.

With reference to FIG. 1A, the first electrode 22 may be positioned along a left side of the anterior region of the chest adjacent to the sternum. The second electrode 24 may be positioned along a right side of the anterior region of the chest adjacent to the sternum. The distal branches 21, 23 diverge from one another at the connector 25 to enable the electrodes 22, 24 to be spaced apart from one another, once implanted, with an electrode gap 74 there between that has a predetermined spacing such as 1.5 cm to 8.5 cm. The electrode gap 74 represents a spacing between the electrodes 22, 24 when the electrodes 22, 24 are implanted generally parallel to and along opposite sides of the sternum. For example, the electrodes 22, 24 may be spaced equal distances from a midline (FIG. 1A) extending vertically through a patient along a center of the sternum. Optionally, one of the electrodes 22, 24 may be positioned laterally closer to the sternum and midline, while the other of the electrodes 22, 24 is positioned laterally further away from the sternum and midline. The electrodes 22, 24 may be positioned subcutaneously to extend vertically along a region adjacent opposite sides of the sternum that aligns with the heart of the patient for providing a sufficient amount of energy for defibrillation.

Figure 1C:
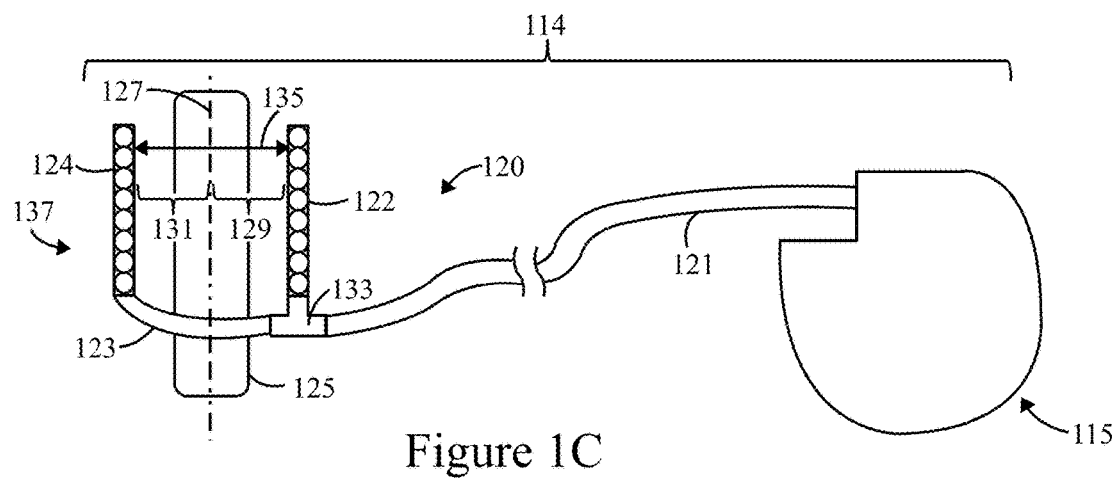
FIG. 1C illustrates an SIMD formed in accordance with embodiments herein.

FIG. 1C illustrates an SIMD 114 formed in accordance with an alternative embodiment. The SIMD 114 includes a pulse generator 115 coupled to a lead 120. The lead 120 includes a lead body 121 that includes a distal portion 137 with a distal electrode 124. The distal electrode 124 is coupled through a distal branch 123 of the lead body 121 to an intermediate electrode 122. The distal branch 123 interconnects the electrodes 124 and 122 in a generally U-shaped alignment when the electrodes 122, 124 are implanted along a generally common implant direction.

In the example of FIG. 1C, a graphical illustration is presented to show an example sternum 125 that extends along a midline 127. The electrodes 122, 124 may be located on opposite sides of the sternum 125 and oriented parallel to the midline 127. The electrodes 122, 124 are spaced apart by a predetermined spacing 135 and are implanted to be oriented vertically in a common direction with the sternum 125. The electrodes 122, 124 may be shifted left or right by various degrees relative to the midline 127 of the sternum 125. The electrodes 122, 124 are spaced lateral distances 129, 131, respectively, from the midline 127. The lateral distances 129, 131 may be equal to one another and/or differ from one another. For example, the electrode 122 may be positioned further away from the midline 127 of the sternum 125, as compared to the spacing of the electrode 124, such that the lateral distance 129 is greater than the lateral distance 131. As another example, the electrode 124 may be positioned further away from the midline 127 of the sternum 125, as compared to the spacing of the electrode 122, such that the lateral distance 131 is greater than the lateral distance 129. The electrode 122 may join the lead body 121 at an intermediate connection 133 in various manners. For example, the intermediate connection 133 may be formed as a Y connection, T connection and the like.

Figure 1D:
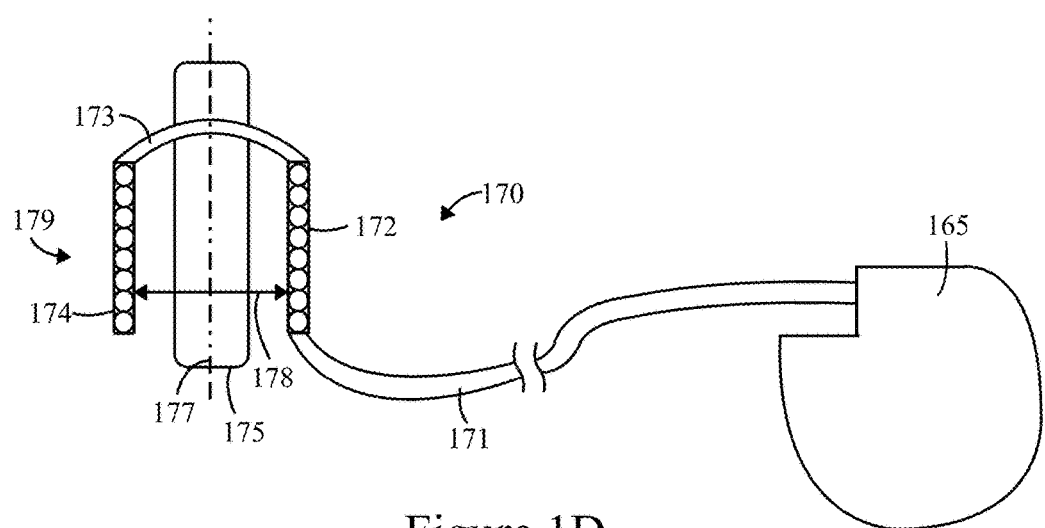
FIG. 1D illustrates an SIMD formed in accordance with embodiments herein.

FIG. 1D illustrates an SIMD formed 154 formed in accordance with an alternative embodiment. The SIMD includes 154 includes a pulse generator 165 coupled 155 coupled to a lead 170. The lead 170 includes a lead body 171 having first and second electrodes 172 and 174 formed in a monotonic unitary manner therewith. The lead 170 is formed with the first electrode 172 at an intermediate point along the lead body 171 in an in-line arrangement with the second electrode 174. The first electrode 172 includes a proximal end that joins the base segment of the lead body 171. The first electrode 172 includes a distal end that joins an intermediate segment 173 of the lead body 171. The intermediate segment 173 interconnects the first and second electrodes 172 and 174 in a generally straight line.

During an implant operation, the lead 170 is inserted such that the first electrode 172 is located generally parallel to a midline 177 of the sternum 175 and spaced a first distance from the midline 177, while the second electrode 174 is also generally parallel to the midline 177 of the sternum and spaced a second distance from the midline 177. The first and second electrodes 172 and 174 are spaced apart from one another by a predetermined spacing 185 (e.g., 1.5 cm to 8.5 cm). The first and second electrode 172 and 174 may be located both on a left side, both on a right side or on opposite sides of the sternum 175. The lead 170 is bent such that the first and second electrodes 172 and 174, and the intermediate segment 173 form generally a U-shape.

Figure 1E:
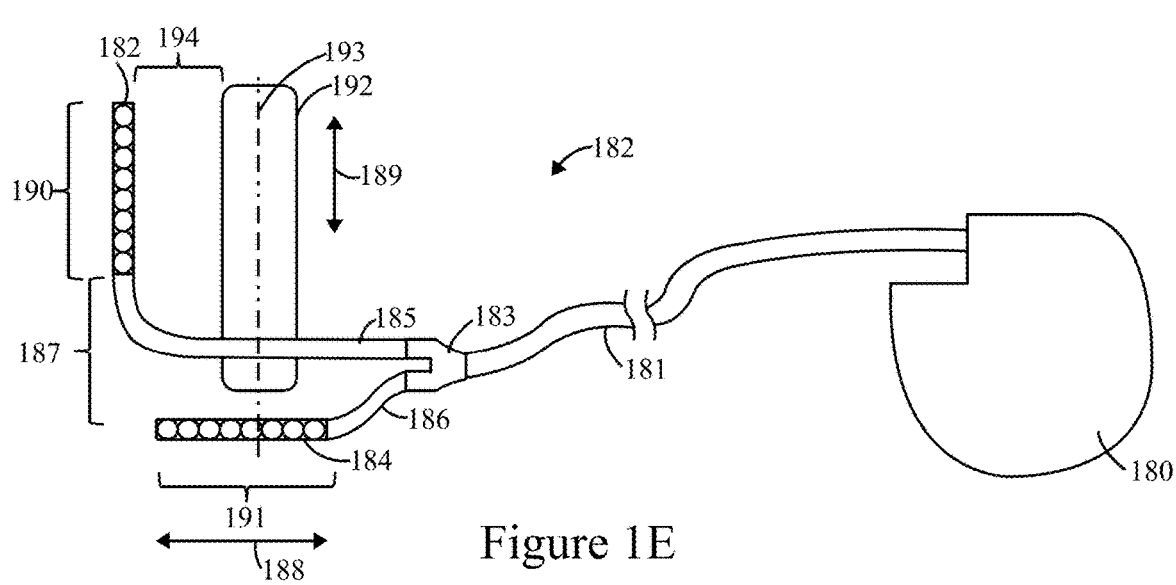
FIG. 1E illustrates an SIMD formed in accordance with embodiments herein.

FIG. 1E illustrates an SIMD formed in accordance with an alternative embodiment. The SIMD includes a pulse generator 180 connected to a lead 182. The lead 182 includes a lead body 181 having a proximal end connected to a header of the PG 180. The lead body 181 includes a splitting connector 183 located at an intermediate point along a length of the lead body 181. The lead 182 includes a parasternal branch 185 and an anterior branch 186 that extend from the splitting connector 183. Distal ends of the parasternal and anterior branches 185 and 186 include first and second electrodes 182 and 184, respectively. The first and second electrodes 182 and 184 may also be referred to as a parasternal electrode and an anterior electrode, respectively, to be indicative of the implant locations of the electrodes. The first and second electrodes 182 and 184 are elongated to extend along corresponding longitudinal axes and have corresponding active lengths 190 and 191. The first electrode 182 may have an active length of 7.0 cm to 11.0 cm, and more specifically between 8.0 cm and 10.0 cm. The second electrode 184 may have an active length of 5.0 cm to 6.5 cm, and more specifically between 5.8 cm and 6.2 cm. However, it is understood that the active lengths of the first and second electrodes 182 and 184 may vary based on various criteria.

During an implant operation, the first (parasternal) electrode 182 is positioned at a parasternal location proximate to a left or right side of the sternum 192 and spaced a lateral spacing 194 from a midline 193 of the sternum 192. The first electrode 182 is oriented to extend generally in a common direction (e.g., parallel) to the midline 193. The first electrode 182 may be shifted vertically up or down along a vertical direction 189 along the sternum 195 to a desired vertical position relative to the heart. The parasternal branch 185 extends from the splitting connector 183 to a proximal end of the first electrode 182.

The second (anterior) electrode 184 is positioned at an anterior location proximate to a lower tip of the sternum 192. The second electrode 184 second electrode 184 is positioned relative to the first electrode 182, such as spacing the second electrode 184 a vertical spacing 187 from a lower/proximal end of the first electrode 182. Optionally, the second electrode 184 may be positioned relative to a lower tip of the sternum such as spacing the second electrode 184 a vertical spacing below the lower tip of the sternum. The second electrode 184 is shifted left/right in a lateral direction 188 to a desired position relative to one or both of the midline 193 of the sternum 192 and/or a longitudinal axis of the first electrode 182.

Figure 2:
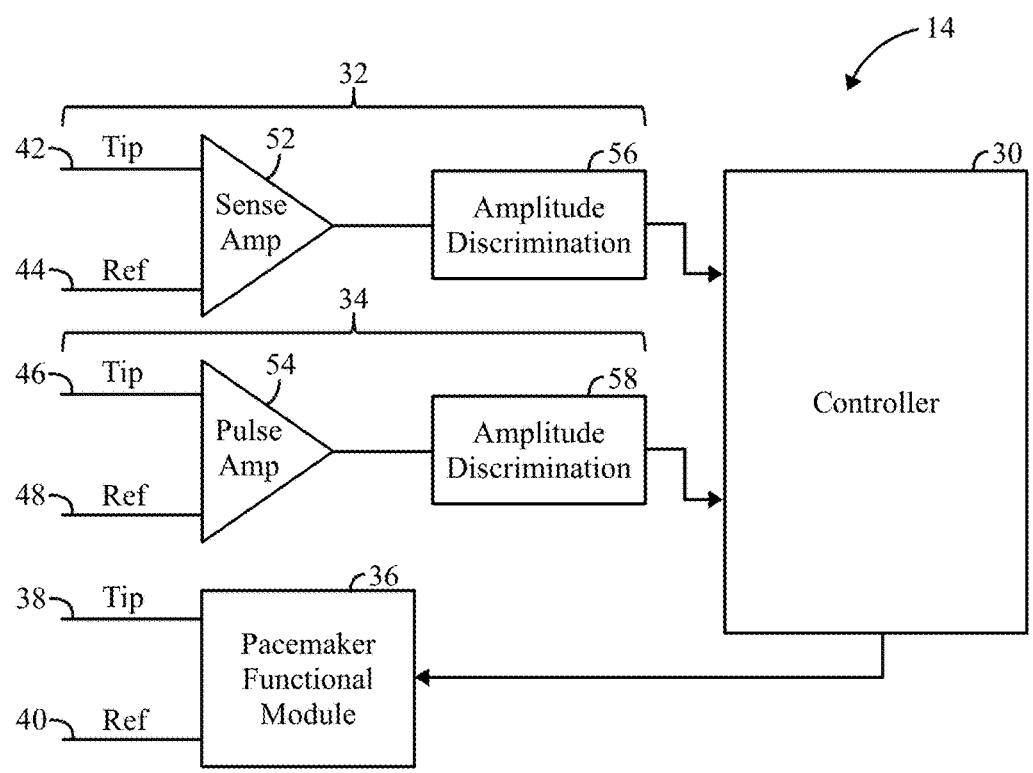
FIG. 2 illustrates a simple block diagram of at least a portion of the circuitry within the SIMD in accordance with embodiments herein.

FIG. 2 illustrates a simple block diagram of at least a portion of the circuitry within the SIMD 14. The SIMD 14 includes a controller 30 that may be coupled to cardiac sensing circuitry 32 and pulse sensing circuitry 34. The controller 30 also utilizes or communicates with various other electronic components, firmware, software, and the like that generally perform sensing and pacing functions (as generally denoted by a pacemaker functional block 36). While the examples herein are provided for pacing and defibrillation functions, the SIMD could be programmed to perform anti-tachycardia pacing, cardiac rhythm therapy, and the like. The cardiac sensing circuitry 32 is configured to detect cardiac events. The pulse sensing circuitry 34 is configured to detect event markers.

The controller 30 is configured to analyze incoming paced cardiac events (as sensed over the cardiac sensing circuitry 32). Based on this analysis, the controller 30 in the SIMD 14 may perform various pacemaker related actions, such as setting or ending timers, recording data, delivery of therapy, and the like. The controller 30 of the SIMD 14 may also perform various cardioversion/defibrillation related functions. In the example of FIG. 2, outputs 38 and 40 represent output terminals that are coupled through a switching circuit (in the functional module 36) to corresponding electrodes on the housing of the SIMD 14. Alternatively, the outputs 38 and 40 may be coupled to respective electrodes on along the lead 20 (FIG. 1).

Inputs 42-48 are provided to the cardiac and pulse sensing circuitry 32 and 34. By way of example, with reference to SIMD 14, inputs 42 and 44 may be coupled to sensing electrodes that supply sensed signals to a sensing amplifier 52. Inputs 46 and 48 may be coupled to the same or different sensing electrodes to provide sensed signals to a pulse amplifier 54. An output of the sensing amplifier 52 is supplied to amplitude discriminator 56, while an output of the pulse amplifier 54 is supplied to amplitude discriminator 58. Outputs of the amplitude discriminators 56 and 58 are then provided to the controller 30 for subsequent analysis and appropriate actions. The inputs 42 and 44 may be coupled to various combinations of the electrodes 22, 24 or the PG electrode 19.

Figure 3A:
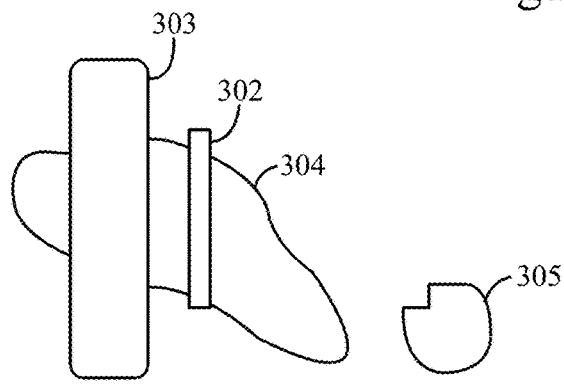
FIG. 3A illustrates a graphical representation of a conventional configuration that includes a pulse generator and an electrode in accordance with embodiments herein.

FIG. 3A illustrates a graphical representation of a conventional configuration that includes a pulse generator 305 and an electrode 302. The pulse generator 305 is located at an anterior position along the left side of the rib cage under the left arm and proximate to an apex of the heart 304. The electrode 302 has a 10 cm active length and is positioned in a frontal chest region proximate the sternum 303 and on the left side of the sternum 303.

Figure 3B:
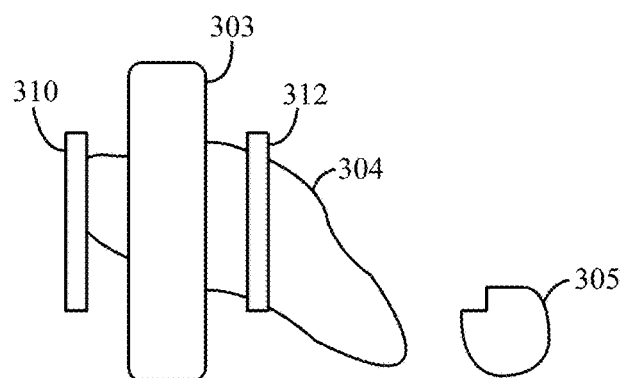
FIG. 3B illustrates graphical representations of SIMD configurations implemented in accordance with embodiments herein.

FIGS. 3B-3F illustrate graphical representations of SIMD configurations implemented in accordance with embodiments herein. FIG. 3B illustrates a new configuration with the pulse generator 305 located at an anterior position along the left side of the rib cage under the left arm (similar to the conventional configuration of FIG. 3A). Unique to the new embodiment of FIG. 3B, dual parasternal electrodes 310 and 312 are located on opposite left/right sides of the sternum 303 and spaced apart from one another by 7.0 cm. The electrodes 310 and 312 each include active lengths of 10 cm.

Figure 3C:
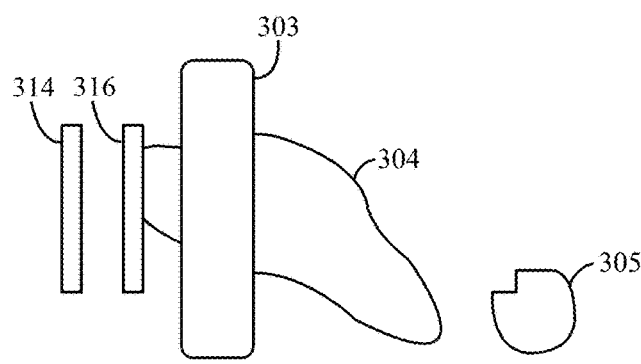
FIG. 3C illustrates graphical representations of SIMD configurations implemented in accordance with embodiments herein.

FIG. 3C illustrates a new configuration with the pulse generator 305 located at an anterior position along the left side of the rib cage under the left arm. Unique to the new embodiment of FIG. 3C, dual parasternal electrodes 314 and 316 are both located on the right side of the sternum 303 and spaced apart from one another by 2.0 cm. The electrodes 314 and 316 each include active lengths of 10 cm.

Figure 3D:
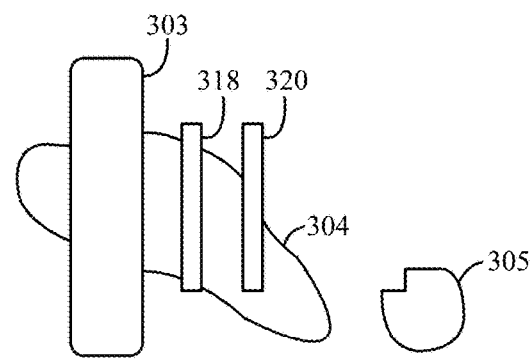
FIG. 3D illustrates graphical representations of SIMD configurations implemented in accordance with embodiments herein.

FIG. 3D illustrates a new configuration with the pulse generator 305 located at an anterior position along the left side of the rib cage under the left arm. Unique to the new embodiment of FIG. 3D, dual parasternal electrodes 318 and 320 are both located on the left side of the sternum 303 and spaced apart from one another by 2.0 cm. The electrodes 318 and 320 each include active lengths of 8 cm.

Figure 3E:
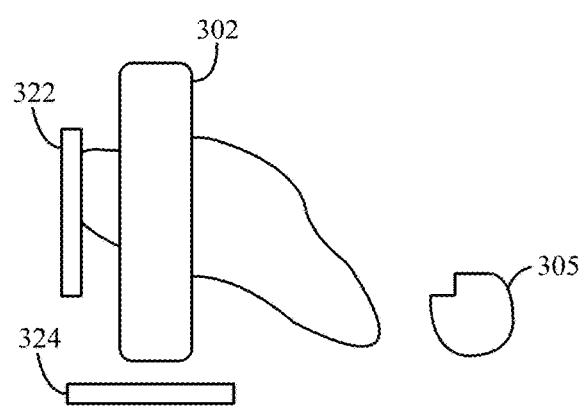
FIG. 3E illustrates graphical representations of SIMD configurations implemented in accordance with embodiments herein.

FIG. 3E illustrates a new configuration with the pulse generator 305 located at an anterior position along the left side of the rib cage under the left arm. Unique to the new embodiment of FIG. 3D, a parasternal electrode 322 is located on the right side of the sternum 303 in combination with an anterior electrode 324 that is located below the sternum 303. The anterior electrode 324 is spaced apart 2 cm below a lower end of the parasternal electrode 322. The parasternal and anterior electrodes 322 and 324 are oriented generally perpendicular to one another in an L-shape. The electrodes 322 and 324 include active lengths of 10 cm and 6 cm, respectively.

Figure 3F:
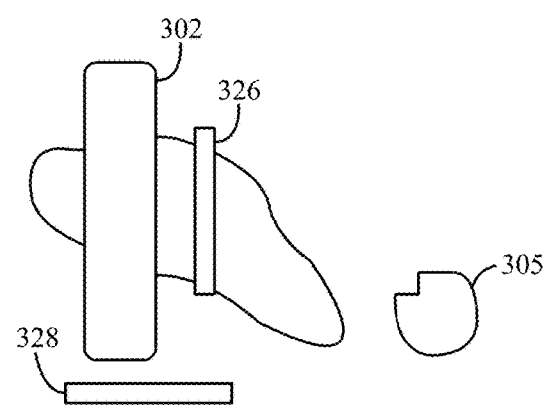
FIG. 3F illustrates graphical representations of SIMD configurations implemented in accordance with embodiments herein.

FIG. 3F illustrates a new configuration with the pulse generator 305 located at an anterior position along the left side of the rib cage under the left arm. Unique to the new embodiment of FIG. 3F, a parasternal electrode 326 is located on the left side of the sternum 303 in combination with an anterior electrode 328 that is located below the sternum 303. The anterior electrode 328 is spaced apart 2 cm below the parasternal electrode 326. The parasternal and anterior electrodes 326 and 328 are oriented generally perpendicular to one another in an L-shape. The electrodes 326 and 328 include active lengths of 10 cm and 6 cm, respectively.

The conventional configuration of FIG. 3A and the new configurations of FIGS. 3B-3F were modeled through computer simulations to identify stimulation characteristics. Table 1 below illustrates the results of the computer simulations, including defibrillation thresholds (DFTs) in Joules (J), current defibrillation thresholds (IDFTs) in amps (A), impedance (Z) in ohms, and PT(V) 0.02% mass. In table 1, row/case #1 corresponds to the conventional configuration described above in connection with FIG. 3A. The computer simulations indicated that the DFTs would be 24 jewels, DFT current 10.2 A, impedance 68 ohms and PT (V) 30.

TABLE 1

| Case # | Configurations | DFT(J) | IDFT(A) | Z(ohms) | PT (V) 0.02% Mass |
|---|---|---|---|---|---|
| 1 | 10 cm sternal coil (left) to CAN (Control) | 24 | 10.2 | 68 | 30 |
| 2 | 10 cm sternal dual coils R&L (7 cmsp) to CAN | 12 | 9.8 | 50.5 | 28 |
| 3 | 10 cm sternal dual coils 2 cmsp Right-> CAN | 14.7 | 9 | 60 | 31 |
| 4 | 8 cm sternal dual coils 2 cmsp Left -> CAN | 20 | 10 | 64 | 28 |
| 5 | 10 cm sternal R + ant 6 cm 1 cmsp (L-shaped) to CAN | 16 | 10.1 | 56.2 | 31 |
| 6 | 10 cm sternal Left + ant 6 cm 2 cmsp (L-shaped) to CAN | 21.7 | 12.2 | 54 | 30 |

Row/case #2 corresponds to a new dual parasternal configuration described above in connection with FIG. 3B. The computer simulations indicated that, when dual parasternal 10 cm active coil electrodes are located on the right and left sides of the sternum at a 7 cm spacing, the DFTs would be 12 joules, DFT current 9.8 A, impedance 50.5 ohms and PT (V) 28. Row/case #3 corresponds to another new dual parasternal configuration described above in connection with FIG. 3C. The computer simulations indicated that, when dual parasternal 10 cm active coil electrodes are located both on the right side of the sternum at a 2 cm spacing, the DFTs would be 14.7 joules, DFT current 9.0 A, impedance 60 ohms and PT (V) 31. Row/case #4 corresponds to another new dual parasternal configuration described above in connection with FIG. 3D. The computer simulations indicated that, when dual parasternal 8 cm active coil electrodes are located both on the left side of the sternum at a 2 cm spacing, the DFTs would be 20.0 joules, DFT current 10.0 A, impedance 64 ohms and PT (V) 28.

Row/case #5 corresponds to a new combination parasternal-anterior configuration described above in connection with FIG. 3E. The computer simulations indicated that, when a parasternal 10 cm active coil electrode is located on the right side of the sternum and a 6 cm active coil electrode is located at an anterior position spaced 1 cm below the parasternal electrode, the DFTs would be 16.0 joules, DFT current 10.1 A, impedance 56.2 ohms and PT (V) 31. Row/case #6 corresponds to another combination parasternal-anterior configuration described above in connection with FIG. 3F. The computer simulations indicated that, when a parasternal 10 cm active coil electrode is located on the left side of the sternum and a 6 cm active coil electrode is located at an interior position spaced 2 cm below the parasternal electrode, the DFTs would be 21.7 joules, DFT current 12.0 A, impedance 54 ohms and PT (V) 30.

From Table 1, it can be seen that the new configurations proposed in accordance with embodiments herein provide substantial unexpected improvements over the conventional configuration. For example, the configuration of case 2 (FIG. 3B) defines a shocking vector that provides a substantially lower defibrillation threshold (12 J v 24 J) as compared to the conventional configuration (case 1). The reduction in defibrillation thresholds was due in part to a substantial decrease in the impedance experienced across the shocking vector (50.5 ohms v 68 ohms) between the electrodes and the PG housing. As further examples, cases 3 and 8 (corresponding to FIGS. 3C and 3E) define shocking vectors that provide substantially lower defibrillation thresholds (14.7 J and 16 J) as compared to the defibrillation threshold of the conventional configuration (24 J in case 1). Again, the reduction in DFTs was in part due to a reduction in the impedance experienced across the shocking vectors (60 ohms and 56.2 ohms, respectively) between the housing of the SIMD and the combination of electrodes (e.g., dual parasternal or parasternal in case 3 and anterior in case 8).

Figure 4:
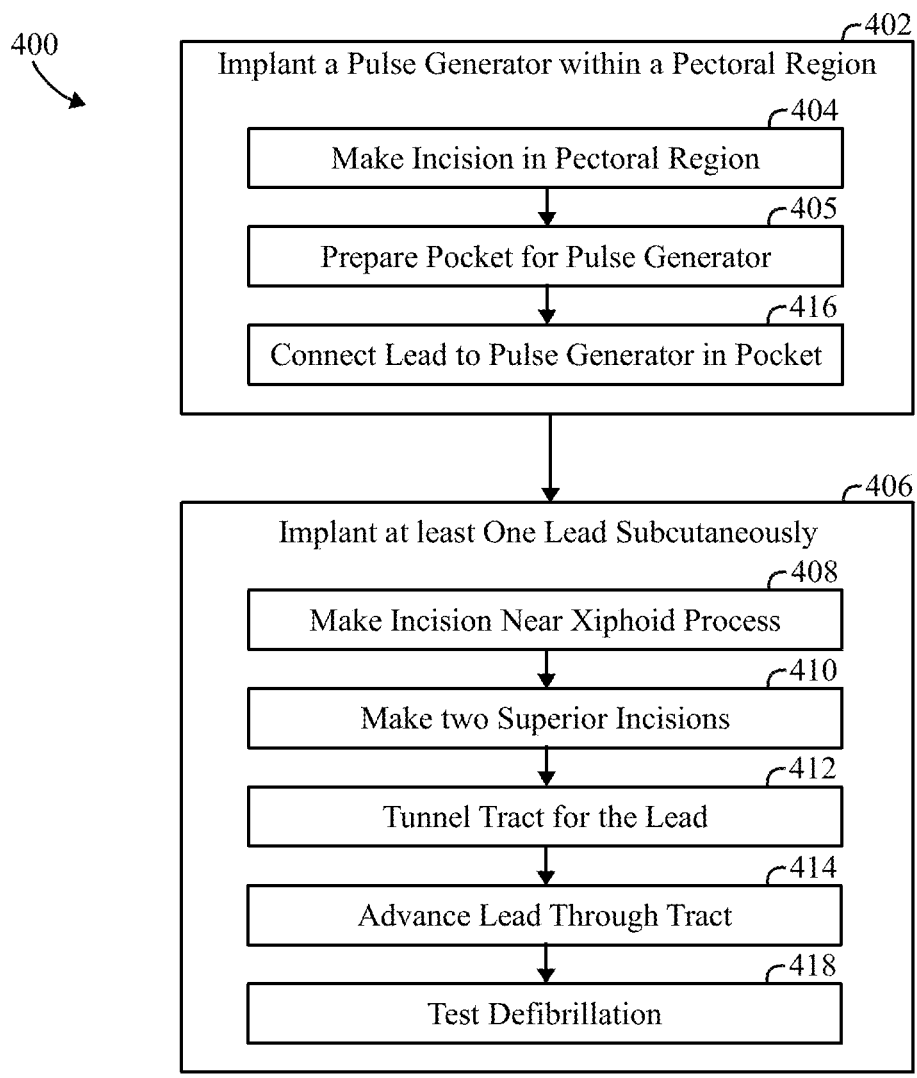
FIG. 4 illustrates a flow chart of a method for implanting a subcutaneous implantable medical system in accordance with embodiments herein.

FIG. 4 illustrates a flow chart of a method 400 for implanting a subcutaneous implantable medical system in accordance with an embodiment. The subcutaneous implantable medical system may be similar or identical to the subcutaneous implantable medical systems described herein. The method 400 includes implanting, at 402, a pulse generator (PG) subcutaneously within a lateral region of the chest, such as along the left side of the rib cage under the left arm. For example, an incision is made to place the pulse generator at the mid-axillary line between the $5^{th}$ and $6^{th}$ intercostal spaces. The SIMD 14 may be positioned relative to a vertical direction substantially aligned with the apex of the heart. The SIMD 14 is configured to deliver various arrhythmia therapies, such as defibrillation therapy, pacing therapy, antitachycardia pacing therapy, cardioversion therapy, and the like. The PG has a housing that includes a PG electrode.

At 405, a pocket may be formed. The pocket may be subcutaneous or submuscular. The pocket may be completed before or after positioning the lead as described below. For subcutaneous pockets, the subcutaneous tissue may be dissected or separated from the pectoral fascia using a designated tool (e.g., knife). In some embodiments, an inflatable balloon may be inserted through the incision and inflated to displace the subcutaneous tissue. For submuscular pockets, the transverse muscle fibers of the pectoralis major may be separated for providing access in front of the pectoralis minor. The pulse generator may be positioned within the pocket before or after lead placement.

The method also includes implanting, at 406, at least one lead having first and second electrodes. Access incisions may be used to manipulate the lead for placing the first and second electrodes at designated positions. The implanting, at 406, may include making an access incision at a xiphoid location, at 408 and, optionally, making one or two other access incisions at 410. The access incision made at 408 may be proximate to a bottom of the sternum. The access incision(s) made at 410 may be located near a top of the sternum (e.g., superior incisions). From the xiphoid incision, two additional tunnels are made to the superior incisions that can be on either the left or right check or on both the left and right chest for parasternal coil electrodes.

Implanting, at 406, may also include tunneling, at 412, a tract between the different incisions and advancing the lead through the tract. For example, a tunneling device (e.g., elongated tube) may be inserted through the first access incision. For example, at 408, the first access incision may be located at a point near a bottom of the sternum along a side of the sternum where the electrode is to be positioned (e.g., on the left or right side of the sternum). The tunneling device separates the subcutaneous tissue from underlying tissue (e.g., muscle, bone) between the first access incision and the pocket in the lateral region below the left arm. When an end of the tunneling device is accessible through the pocket, a distal end of the lead may be coupled to the end of the tunneling device (e.g., through a suture loop). The tunneling device is then withdrawn from the first access incision, at 414, thereby pulling the lead through the newly-formed tract between the pocket and the first access incision. In accordance with some embodiments, the splitting connector (e.g., Y-connector) will be used to connect two parasternal coil electrodes at the xiphoid incision to the lead body.

Previously or subsequently, another tunneling device may be inserted through a second access incision (at 410), such as at a point near an upper end of the sternum and on the corresponding left or right side of the sternum where the distal end of the parasternal electrode is to terminate. At 412, the tunneling device is advanced downward along a path generally parallel to the sternum toward the first access incision along a corresponding side of the sternum. When the end of the tunneling device is accessible through the first access incision, the lead may be coupled to the end of the tunneling device. The tunneling device is then withdrawn from the second access incision, thereby pulling the lead through the newly-formed tract between the first access incision and the second access incision. This process may be repeated as necessary for positioning a second parasternal electrode on the same or an opposite side of the sternum and/or for an anterior electrode located below the sternum. It is understood that for an anterior electrode, the first access incision may be sufficient to pull the interior electrode to the final termination point, without the need for a second access incision.

Optionally, when using dual parasternal electrodes, the pair of parasternal electrodes may be pulled through the first access incision at the same time, such as when formed as part of a single lead body. Optionally, when separate leads are used for the dual parasternal electrodes, the separate leads may be pulled through a common first access incision at the same time and/or through separate first and second access incisions at different times. After positioning the first and second electrodes, the pulse generator may be connected to the lead. More specifically, an end portion of the lead with contacts may be inserted into one or more terminal ports on a header of the pulse generator.

At 418, a defibrillation test may be performed to determine a defibrillation threshold. The defibrillation threshold is a quantitative estimate of the ability of the heart to defibrillate. The defibrillation threshold is typically defined as the minimum shock strength that causes defibrillation. The defibrillation threshold can be measured by changing the voltages in subsequent VF inductions in accordance with a predetermined protocol. For example, the stored voltages may be incrementally decreased for subsequent VF inductions until the first shock is unable to defibrillate. If a high defibrillation threshold is identified, it may be desirable to make adjustments to the system. For example, the lead could be repositioned, the lead could be switched-out, portions of the electrodes could be capped, or another lead may be added.

Figure 5:
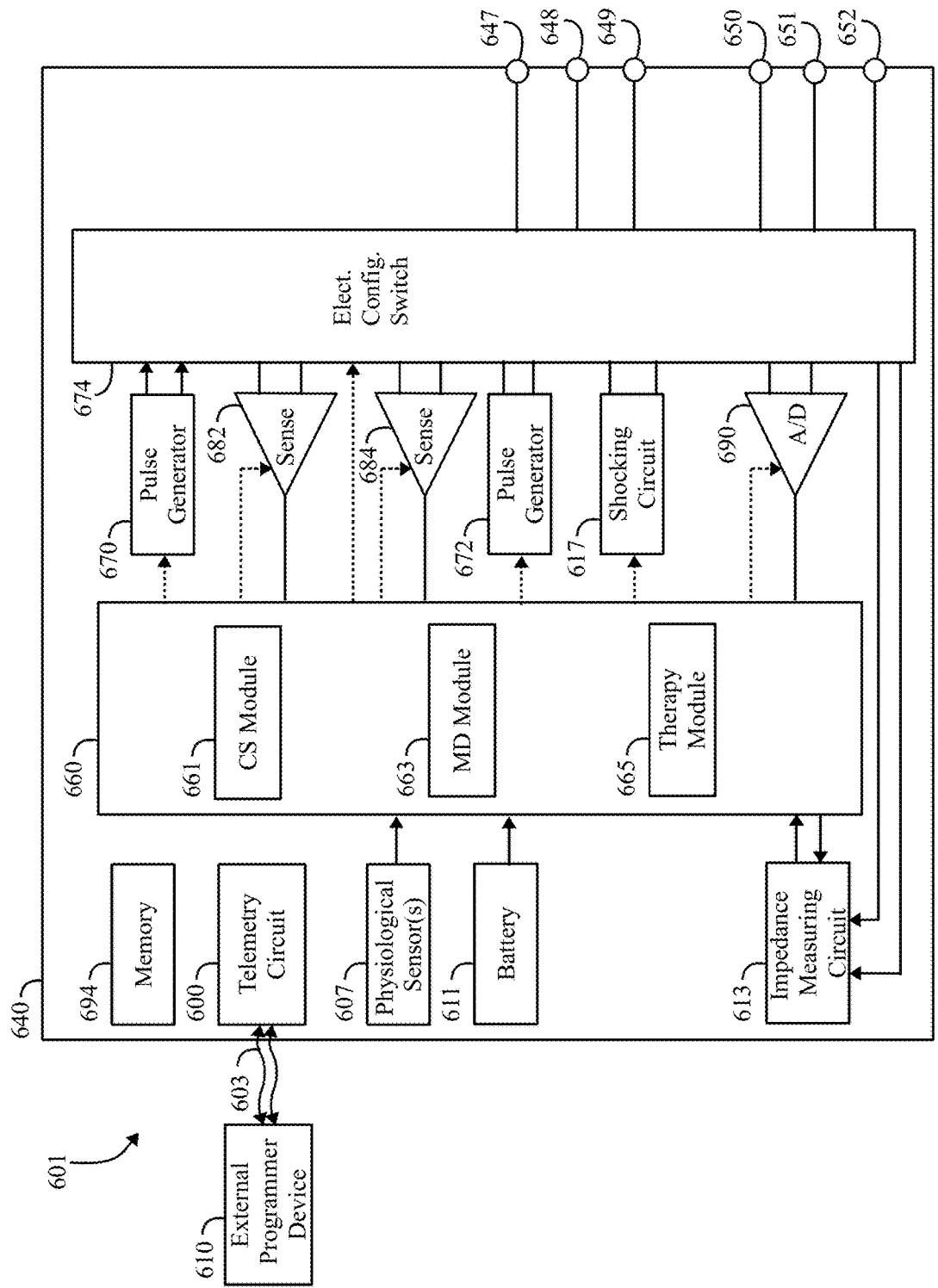
FIG. 5 illustrates a block diagram of an SIMD in accordance with embodiments herein.

FIG. 5 illustrates a block diagram of an SIMD 601. The SIMD 601 is capable of performing stimulation therapy, including cardioversion, defibrillation, and pacing stimulation. The SIMD 601 is hereinafter referred to as the device 610. While a particular multi-element device is shown, this is for illustration purposes only. It is understood that the appropriate circuitry could be duplicated, eliminated or disabled in any desired combination to provide a device capable of monitoring impedance and/or cardiac signals, and/or treating the appropriate chamber(s) with cardioversion, defibrillation and pacing stimulation.

The housing 640 for the device 610 is often referred to as the "canister," "can," "case," or "case electrode" and may be programmably selected to act as the shock electrode and/or as a return electrode for some or all sensing modes. The housing 640 may further be used as a return electrode alone or in combination with one or more other electrodes. The housing 640 further includes a connector (not shown) having a plurality of terminals 647-652. To achieve sensing, pacing, and shocking in connection with desired chambers of the heart, the terminals 647-652 are selectively connected to corresponding combinations of electrodes.

The device 610 includes a programmable microcontroller 660 that controls the various modes of sensing and stimulation therapy. The microcontroller 660 includes a microprocessor, or equivalent control circuitry, designed specifically for controlling sensing impedance derivation and the delivery of stimulation therapy and may further include RAM or ROM memory, logic and timing circuitry, state machine circuitry, and I/O circuitry. The microcontroller 660 includes the ability to process or monitor input signals (data) as controlled by a program code stored in memory. The details of the design and operation of the microcontroller 660 are not critical to the present invention. Rather, any suitable microcontroller 660 may be used.

The microcontroller 660 includes inputs that are configured to collect cardiac signals associated with electrical or mechanical behavior of a heart over at least one cardiac cycle. The cardiac signals may be from the cardiac sensing circuit 682 and representative of electrical behavior of the heart. The circuit 682 may provide separate, combined, composite or difference signals to the microcontroller 660 representative of the sensed signals from the electrodes. Optionally, the cardiac signals may be the output of the A/D circuit 690 that are representative of electrical behavior of the heart. The cardiac signals may be the output of the physiologic sensor 607 that are representative of mechanical behavior.

The microcontroller 660 includes a cardiac signal (CS) module 661, a marker detection (MD) module 663 and a therapy module 665 (among other things). The CS module 661 is configured to analyze cardiac signals. The MD module 663 is configured to analyze signals sensed over the marker sensing channel and identify incoming event markers. The therapy module 665 is configured to modulate, over multiple cardiac cycles; at least one therapy parameter while the device 610 obtains a collection of at least one CSF indicators associated with different therapy parameters. The therapy module 665 is further configured to adjust a therapy configuration based on, among other things, the cardiac signals and based on the event markers.

The microcontroller 660 further controls a shocking circuit 617 by way of a control signal. The shocking circuit 617 generates stimulating pulses of low (up to 0.5 Joules), moderate (0.5-10 Joules), or high energy (11 to 50 Joules), as controlled by the microcontroller 660. Stimulating pulses may be applied to the patient's heart through at least two shocking electrodes.

One or more pulse generators 670 and 672 generate various types of therapy, such as pacing and ATP stimulation pulses for delivery by desired electrodes. The electrode configuration switch 674 (also referred to as a switch bank) controls which terminals 647-652 are connected to the pulse generators 670, 672, thereby controlling which electrodes receive a therapy. The pulse generators, 670 and 672, may include dedicated, independent pulse generators, multiplexed pulse generators, shared pulse generators or a single common pulse generator. The pulse generators 670 and 672 are controlled by the microcontroller 660 via appropriate control signals to trigger or inhibit stimulation pulses. The microcontroller 660 further includes timing control circuitry which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

An electrode configuration switch 674 connects the sensing electronics to the desired terminals 647-652 of corresponding sensing electrodes. For example, a portion of the terminals may be coupled to electrodes configured to define a sensing and/or shocking vector that passes through the left ventricle. The switch 674 may connect terminals to the event marker sensing circuit 684 (which corresponds to the event marker sensing channel) and the microcontroller. The circuit 684 may amplify, filter, digitize and/or otherwise process the sensed signals from the select electrodes.

The switch 674 also connects various combinations of the electrodes to an impedance measuring circuit 613. The impedance measuring circuit 613 includes inputs to collect multiple measured impedances between corresponding multiple combinations of electrodes. For example, the impedance measuring circuit 613 may collect a measured impedance for each or a subset of the active sensing vectors. Optionally, the impedance measuring circuit 613 may measure respiration or minute ventilation; measure thoracic impedance for determining shock thresholds; detect when the device has been implanted; measure stroke volume; and detect the opening of heart valves, etc.

The switch bank 674 includes a plurality of switches for connecting the desired electrodes to the appropriate I/O circuits, thereby providing complete electrode programmability. The switch 674, in response to a control signal from the microcontroller 660, determines the polarity of the stimulation pulses (e.g., unipolar, bipolar, co-bipolar, etc.) by selectively closing the appropriate combination of switches (not specifically shown). The outputs of the cardiac signal and event marker sensing circuits 682 and 684 are connected to the microcontroller 660 which, in turn, is able to trigger or inhibit the pulse generators 670 and 672, respectively. The sensing circuits 682 and 684, in turn, receive control signals from the microcontroller 660 for purposes of controlling the gain, threshold, the polarization charge removal circuitry (not shown), and the timing of any blocking circuitry (not shown).

Cardiac signals are also applied to the inputs of an analog-to-digital (A/D) data acquisition system 690. The data acquisition system 690 is configured to acquire cardiac signals, convert the raw analog data into a digital signal, and store the digital signals for later processing and/or telemetric transmission to an external device. The data acquisition system 690 samples cardiac signals across any pair of desired electrodes. The data acquisition system 690 may be coupled to the microcontroller 660, or other detection circuitry, for detecting an evoked response from the heart in response to an applied stimulus, thereby aiding in the detection of "capture." Capture occurs when an electrical stimulus applied to the heart is of sufficient energy to depolarize the cardiac tissue, thereby causing the heart muscle to contract.

The microcontroller 660 is further coupled to a memory 694 by a suitable data/address bus 696. The memory 694 stores programmable operating, impedance measurements, impedance derivation and therapy-related parameters used by the microcontroller 660. The operating and therapy-related parameters define, for example, pacing pulse amplitude, pulse duration, electrode polarity, rate, sensitivity, automatic features, arrhythmia detection criteria, and the amplitude, wave shape and vector of each stimulating pulse to be delivered to the patient's heart within each respective tier of therapy.

The operating and therapy-related parameters may be non-invasively programmed into the memory 694 through a telemetry circuit 600 in telemetric communication with the external device, such as a programmer, trans-telephonic transceiver, or a diagnostic system analyzer. The telemetry circuit 600 is activated by the microcontroller 660 by a control signal. The telemetry circuit 600 advantageously allows data and status information relating to the operation of the device (as contained in the microcontroller 660 or memory 694) to be sent to an external device 101 through an established communication link 603.

The device 610 may include a physiologic sensor 607 to adjust pacing stimulation rate according to the exercise state of the patient. The physiological sensor 607 may further be used to detect changes in cardiac output, changes in the physiological condition of the heart, or diurnal changes in activity (e.g., detecting sleep and wake states). The battery 611 provides operating power to all of the circuits.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

What is claimed is:

1. An implantable medical device (IMD), comprising:
   a pulse generator (PG) configured to be positioned within a lateral region of a chest of a patient, the PG having a housing that includes a PG electrode, the PG having an electronics module; and
   an elongated lead that is electrically coupled to the pulse generator, the elongated lead including a first electrode that is configured to be positioned along a first parasternal region proximate a sternum of the patient and a second electrode that is configured to be positioned at an anterior region of the patient, wherein the first and second electrodes are coupled to be electrically common with one another, wherein the electronics module is configured to provide electrical shocks for antiarrhythmic therapy along at least one shocking vector between the PG electrode and the first and second electrodes, wherein the anterior region is located proximate to a lower end of the sternum, the second electrode configured to be oriented to extend in a non-parallel direction relative to a direction of the first electrode, the second electrode located at a position, relative to a midline of the sternum, that is vertically below the first electrode, the first electrode having a length that is greater than a length of the second electrode.

2. The IMD of claim 1, wherein the length of the first electrode is 7.0 cm to 11.0 cm, and the length of the second electrode is 5.0 cm to 6.5 cm.

3. The IMD of claim 1, wherein the pulse generator and first and second electrodes define a shocking vector that provides a defibrillation threshold of at most 20 Joules.

4. The IMD of claim 1, wherein the pulse generator and first and second electrodes define a shocking vector there between that exhibits an impedance along the shocking vector that is no more than 64 ohms.

5. The IMD of claim 1, wherein the pulse generator and first and second electrodes define a shocking vector there between that exhibits an impedance along the shocking vector that is no more than 56.2 ohms.

6. An implantable medical device (IMD), comprising:
a pulse generator (PG) configured to be positioned within a lateral region of a chest of a patient, the PG having a housing that includes a PG electrode, the PG having an electronics module; and
an elongated lead that is electrically coupled to the pulse generator, the elongated lead including a first electrode that is configured to be positioned along a first parasternal region proximate a sternum of the patient and a second electrode that is configured to be positioned at a second parasternal region of the patient, wherein the first and second electrodes are coupled to be electrically common with one another, wherein the electronics module is configured to provide electrical shocks for antiarrhythmic therapy along at least one shocking vector between the PG electrode and the first and second electrodes,
wherein the second electrode configured to be oriented to extend in a common direction with the first electrode and along a midline of the sternum, the first and second electrodes configured to be spaced apart by a distance of between 6.0 cm and 8.5 cm as measured in a direction transverse to the midline of the sternum.

7. The IMD of claim 6, wherein the first and second electrodes are configured to be positioned laterally along adjacent opposite sides of the sternum.

8. The IMD of claim 6, wherein the first and second electrodes are configured to be positioned on a common side of the sternum with the first electrode positioned laterally closer to the sternum, and the second electrode positioned laterally further away from the sternum.

9. The IMD of claim 6, wherein at least one of the first and second electrodes has an active length of 7-11 cm.

10. The IMD of claim 6, wherein the lead includes a lead body having a base segment with a proximal end to be electrically coupled to a header of the PG, the lead including first and second distal branches at a distal end of the lead, the first and second electrodes provided on the first and second distal branches, respectively.

11. The IMD of claim 10, wherein the lead body further comprises a Y-connector connecting the first and second distal branches to a distal end of the base segment.

12. A method comprising:
implanting a pulse generator (PG) within a lateral region of a chest of a patient, the PG having a housing that includes a PG electrode;
implanting at least one lead having first and second electrodes that are coupled to be electrically common with one another, wherein the first and second electrodes are elongated, the implanting comprising:
positioning the first electrode along a first parasternal region proximate to a sternum of the patient and positioning the second electrode at an anterior region of the patient; and
positioning the second electrode proximate to a lower end of the sternum and orienting the second electrode to extend in a non-parallel direction relative to a direction of the first electrode, locating the second electrode at a position, relative to a midline of the sternum, that is vertically below the first electrode; and
configuring the electronics module to provide electrical shocks for antiarrhythmic therapy along at least one shocking vector between the PG electrode and the first and second electrodes.

13. The method of claim 12, wherein the non-parallel direction orients a longitudinal axis of the second electrode perpendicular to a longitudinal axis of the first electrode.

14. A method comprising:
implanting a pulse generator (PG) within a lateral region of a chest of a patient, the PG having a housing that includes a PG electrode;
implanting at least one lead having first and second electrodes that are coupled to be electrically common with one another, wherein the first and second electrodes are elongated, the implanting comprising positioning the first and second electrodes at a dual parasternal position proximate to a sternum of the patient, extending in a common direction and spaced apart by a distance of 6.0 cm to 8.5 cm; and
configuring the electronics module to provide electrical shocks for antiarrhythmic therapy along at least one shocking vector between the PG electrode and the first and second electrodes.

15. The method of claim 14, further comprising positioning the first and second electrodes laterally along adjacent opposite sides of the sternum.

16. The method of claim 14, further comprising positioning the first and second electrodes on a common side of the sternum with the first electrode positioned laterally closer to the sternum, and the second electrode positioned laterally further away from the sternum.

17. The method of claim 14, wherein at least one of the first and second electrodes has an active length of 8-11 cm.

18. The method of claim 14, wherein the pulse generator is configured to generate a defibrillating energy of at most 40 Joules.

* * * * *